US005962747A

United States Patent [19]

Tokumasu et al.

[11] Patent Number: 5,962,747

[45] Date of Patent: Oct. 5, 1999

[54] PROCESS FOR PRODUCING 1,3-DI-(2-HYDROPEROXY-2-PROPYL) BENZENE

[75] Inventors: Shigefumi Tokumasu; Hideo Ohki; Toshikazu Ohmae, all of Chiba, Japan

[73] Assignee: Sumitomo Chemical Co., Ltd., Osaka, Japan

[21] Appl. No.: 08/956,794

[22] Filed: Oct. 23, 1997

[30] Foreign Application Priority Data

Oct. 23, 1996 [JP] Japan .................................... 8-280870

[51] Int. Cl.[6] .................................................. C07C 409/00

[52] U.S. Cl. ............................................ 568/562; 568/564

[58] Field of Search ..................................... 568/564, 562

[56] References Cited

U.S. PATENT DOCUMENTS

| | | |
|---|---|---|
| 2,915,558 | 12/1959 | Alder . |
| 3,190,924 | 6/1965 | Sodomann . |
| 3,950,431 | 4/1976 | Suda . |
| 4,935,551 | 6/1990 | Wu ......................................... 568/562 |

FOREIGN PATENT DOCUMENTS

| | | |
|---|---|---|
| 5-87056 | 12/1993 | Japan . |
| 7-45462 | 5/1995 | Japan . |

OTHER PUBLICATIONS

Chemical abstracts CA:118:80630 abs of JP04210674, Dec. 1990.

*Primary Examiner*—Gary Geist
*Assistant Examiner*—Jean F Vollano
*Attorney, Agent, or Firm*—Sughrue, Mion, Zinn, Macpeak & Seas, PLLC

[57] ABSTRACT

A process for producing 1,3-di-(2-hydroperoxy-2-propyl) benzene comprising an oxidizing step, an extracting step with an aqueous solution and a recycling step wherein the accumulated equilibrium concentration of 1,3-di-(2-hydroxy-2-propyl)benzene in the circulating oil obtained by an extracting step with an aqueous solution is 4.2% by weight or less. The process enables to avoid inconveniences like occlusion of inside space of an apparatus and failure of detection of measuring machines and allows continuous safe operation.

5 Claims, No Drawings

PROCESS FOR PRODUCING 1,3-DI-(2-HYDROPEROXY-2-PROPYL) BENZENE

BACKGROUND OF THE INVENTION

1. Field of the Invention

The present invention relates to a process for producing 1,3-di-(2-hydroperoxy-2-propyl)benzene (hereinafter, referred to as "DHPO"). More particularly, the present invention relates to a process for producing DHPO, said process allowing successful solution of problems that a by-product, 1,3-di-(2-hydroxy-2-propyl)benzene (hereinafter, referred to as "DCA") causes inconveniences such as occlusion of inside space of an apparatus and failure of detection of measuring machines and that such inconveniences makes a long-term safe operation difficult.

2. Background Information

There has been known a process in which a starting solution containing 1,3-diisopropylbenzene (hereinafter, referred to as "MDC") is subjected to an oxidizing reaction to convert MDC into DHPO and DHPO is then subjected to acid cleavage reaction to produce resorcinol and acetone. The oxidized solution produced contains DHPO, 3-(2-hydroxy-2-propyl)-1-(2-hydroperoxy-2-propyl)benzene (hereinafter, referred to as "CHPO"), 3-isopropyl-1-(2-hydroperoxy-2-propyl)benzene (hereinafter, referred to as "MHPO"), unreacted MDC and a by-product, DCA. Said oxidized solution is subjected to an extraction using an aqueous alkali solution or the like to produce an aqueous layer containing mainly DHPO and CHPO and an oily layer containing mainly MHPO, MDC and DCA. At least part of said oily layer is usually recycled as a circulating oil to the oxidizing reaction step in order to recover MHPO and MDC. In the conventional technique, however, problems arose that DCA as the by-product precipitated at various parts of the system causing inconveniences such as occlusion of inside space of an apparatus and failure of detection of measuring machines and that such inconveniences makes a long-term safe operation difficult.

After extensive studies searching for a process for producing DHPO having no such problems, the present inventors have found that the inconveniences such as occlusion of the inside space of the apparatus and failure of detection of measuring machines does not arise by maintaining the accumulated equilibrium concentration of 1,3-di-(2-hydroxy-2-propyl)benzene (DCA) in the circulating oil at 4.2% by weight or less when the oxidized solution obtained by subjecting the starting solution containing MDC to the oxidizing reaction is subjected to an extraction using an aqueous solution and at least part of the oily layer is recycled as a circulating oil to the starting solution. The present invention has been completed on the basis of such fact.

SUMMARY OF THE INVENTION

Accordingly, the present invention provides a process for producing 1,3-di-(2-hydroperoxy-2-propyl)benzene comprising the following steps:

- an oxidizing step: a step in which a starting solution containing 1,3-diisopropylbenzene is subjected to an oxidizing reaction to produce an oxidized solution containing 1,3-di-(2-hydroperoxy-2-propyl)benzene and a by-product, 1,3-di-(2-hydroxy-2-propyl)benzene,
- an extracting step with an aqueous solution: a step in which said oxidized solution is subjected to an extraction using an aqueous solution to produce an oily layer containing 1,3-di-(2-hydroxy-2-propyl)benzene and an aqueous layer containing 1,3-di-(2-hydroperoxy-2-propyl)benzene, and
- a recycling step: a step in which at least part of said oily layer is recycled as a circulating oil back to the starting solution;

and wherein the accumulated equilibrium concentration of 1,3-di-(2-hydroxy-2-propyl)benzene in the circulating oil is 4.2% by weight or less.

DETAILED DESCRIPTION OF THE INVENTION

The oxidizing step is a step in which a starting solution containing MDC is subjected to an oxidizing reaction to obtain an oxidized solution containing DHPO, CHPO, MHPO, unreacted MDC and DCA as a by-product. The starting solution is not particularly limited but is usually a mixed solution containing 20–60% by weight of MHPO, 10–40% by weight of MDC, 0–5% by weight of DHPO, 0–10% by weight of CHPO and 0–4.2% by weight of DCA. As an oxidizing agent, the air or pure oxygen is usually used. Preferred reaction temperature is 70–100° C. and preferred pressure is 0–1 MPa(G). The residence time is about 0–50 hours. The apparatus used in the oxidizing step includes, for example, flow-type reaction vessel or tower.

It is preferred that the concentration of ingredients contained in the oxidized solution obtained in the oxidizing step is 3–30% by weight of DHPO, 0–10% by weight of CHPO, 20–60% by weight of MHPO, 0–35% by weight of MDC and 0–4.2% by weight of DCA.

The extracting step with an aqueous solution is a step in which the oxidized solution is subjected to extraction with water to obtain an aqueous layer containing DHPO, CHPO and DCA and an oily layer containing MHPO, MDC and DCA.

Since said oily layer is used as an circulating oil in the subsequent recycling step, it is preferred that the concentration of DCA in said oily layer is maintained at a lower level.

The ratio A/B is preferably 330 or more, more preferably 400 or more wherein A is the weight of aqueous solution used in the extracting step with an aqueous solution per unit time and B is the weight of 1,3-di-(2-hydroxy-2-propyl) benzene produced in the whole system per unit time. The accumulated equilibrium concentration of DCA in the circulating oil can be controlled by changing the ratio A/B.

Further, it is preferred that the weight ratio of the aqueous solution and the oily layer (aqueous solution/oily layer) is 0.2–5.

Preferred aqueous solution is an aqueous alkali solution and preferred alkali is sodium hydroxide. The concentration of alkali in the aqueous alkali solution is preferably 0.1–30% by weight. Preferred temperature for extraction is 0–70° C. It is preferred to carry out with 1–10 stages countercurrent extraction. Apparatus used in the extracting step with an aqueous solution includes, for example, a mixer-settler, an extraction tower and the like.

The recycling step is a step in which at least part of the oily layer obtained in the extracting step with an aqueous solution is recycled as a circulating oil to said oxidizing reaction step. As the circulating oil, whole or part of the oily layer obtained in the extracting step with an aqueous solution may be used and usually 90–100% of the oily layer obtained in the extracting step with an aqueous solution is used.

The accumulated equilibrium concentration of DCA in the circulating oil is 4.2% by weight or less and preferably 3.6% by weight or less. The accumulated equilibrium concentration of DCA in the circulating oil refers to the accumulated equilibrium concentration of DCA after the system has come to the stationary state and the non-stationary state at the starting time or quenching time of the system is excluded. When said concentration is over 4.2% by weight, inconveniences such as occlusion of inside space of an apparatus and failure of detection of measuring machines arises.

In the present invention, it is preferred to conduct an extracting step with methyl isobutyl ketone (hereinafter, referred to as "MIBK"), as described below, in addition to the steps illustrated above.

An extracting step with MIBK: a step in which the aqueous layer obtained in the extracting step with an aqueous solution is subjected to extraction with MIBK to produce a MIBK layer containing mainly DHPO, CHPO and DCA and an aqueous layer.

In the extracting step with MIBK, the weight ratio of water to MIBK (water/MIBK) is preferably 0.2–10. Preferred temperature for extraction is 20–80° C. Apparatus used in the extracting step with MIBK includes, for example, a mixer-settler, an extraction tower and the like.

The aqueous layer obtained in the extracting step with MIBK contains extractant component such as alkali used in the extracting step with an aqueous solution described above and reuse of said aqueous layer by recycling to the extracting step with an aqueous layer described above allows recovery of said extractant component and reduction of expenses for waste water treatment.

EXAMPLES

The following Examples further illustrate the present invention in detail but are not to be construed to limit the scope thereof.

Example 1

DHPO was obtained by conducting an oxidizing step in which a starting solution containing MDC is subjected to an oxidizing reaction to obtain an oxidized solution containing DHPO, CHPO, MHPO, unreacted MDC and DCA as a by-product, an extracting step with water in which the oxidized solution is subjected to extraction with an aqueous solution to obtain an aqueous layer containing mainly DHPO, CHPO and DCA and an oily layer containing mainly MHPO, MDC and DCA, a recycling step in which at least part of the oily layer obtained in the extracting step with an aqueous solution is recycled as a circulating oil to said oxidizing reaction step, and an extracting step with MIBK in which the aqueous layer obtained in the extracting step with an aqueous solution is subjected to extraction with MIBK to produce a MIBK layer containing mainly DHPO, CHPO and DCA and an aqueous layer.

The starting solution contained 40% by weight of MHPO, 24% by weight of MDC, 0.3% by weight of DHPO, 3% by weight of CHPO and 2.6% by weight of DCA. As an oxidizing agent, the air was used. The reaction conditions included a temperature of 88° C., a pressure of 0.3 MPa(G) and a residence time of 10 hours. The apparatus used in the oxidizing step was a flow-type reaction vessel.

The weight ratio (water/oil) in the extracting step with the aqueous solution was 0.5 and the aqueous solution was an aqueous sodium hydroxide solution (concentration: 7% by weight). The conditions for extraction included a temperature of 40° C. and the apparatus was a mixer-settler.

In the recycling step, 99.6% of the oily layer obtained in the extracting step with the aqueous solution was used.

The weight ratio (water/oil) in the extracting step with MIBK was 0.6–5. The conditions for extraction included a temperature of 20–60° C. and the apparatus was an extraction tower.

The accumulated equilibrium concentration of DCA in the circulating oil was 2.6% by weight. The value A/B was 820.

As the result, no inconveniences like occlusion of inside space of an apparatus and failure of detection of measuring machines arose and continuous operation was possible.

Example 2 and Comparative Example 1

The procedure in Example 1 was substantially repeated except conditions shown in Table 1. The results are shown in Table 1.

TABLE 1

| | Example 1 | Example 2 | Comparative Example 1 |
|---|---|---|---|
| Conditions | | | |
| Accumulated equilibrium concentration of DCA, wt % *1 | 2.6 | 3.6 | 4.3 |
| A T/H | 36 | 36 | 38 |
| B T/H | 0.044 | 0.090 | 0.120 |
| A/B*2 | 820 | 400 | 320 |
| Results Presence or absence of occlusion etc. *3 | Absent | Absent | Present |

*1 Accumulated equilibrium concentration of DCA in the circulating oil
*2 B was calculated from the weight of oxidized oil and extracted oil with MIBK and the results analyzing thereof.
*3 Presence or absence of occlusion of inside space of the apparatus and failure of detection of measuring machines because of precipitation of DCA at various sites in the system

What is claimed is:

1. A process for producing 1,3-di-(2-hydroperoxy-2-propyl)benzene comprising the following steps:

an oxidizing step in which a starting solution containing 1,3-diisopropylbenzene is subjected to an oxidizing reaction to produce an oxidized solution containing 1,3-di-(2-hydroperoxy-2-propyl)benzene and a 1,3-di-(2-hydroxy-2-propyl)benzene by-product, an extracting step in which said oxidized solution is subjected to an extraction using an aqueous alkali solution to produce an oily layer containing 1,3-di-(2-hydroxy-2-propyl)benzene and an aqueous layer containing 1,3-di-(2-hydroperoxy-2-propyl)benzene, and a recycling step in which at least part of said oily layer is recycled as a circulating oil back to the starting solution;

further comprising controlling the ratio A/B to 330 or more, wherein A is the weight of the aqueous alkali solution used in the extracting step per unit time and B is the weight of 1,3-di-(2-hydroxy-2-propyl)benzene by-product produced in the oxidizing step and extracting step per unit time, such that the accumulated equilibrium concentration of 1,3-di-(2-hydroxy-2-propyl)benzene in the circulating oil is 3.6% by weight or less, wherein the weight percentage is based on the total weight of the circulating oil.

2. A process for producing 1,3-di-(2-hydroperoxy-2-propyl)benzene comprising the following steps:

an oxidizing step in which a starting solution containing 1,3-diisopropylbenzene is subjected to an oxidizing reaction to produce an oxidized solution containing 1,3-di-(2-hydroperoxy-2-propyl)benzene, 3-(2- hydroxy-2-propyl)-1-(2-hydroperoxy-2-propyl) benzene, 3-isopropyl-1-(2-hydroperoxy-2-propyl) benzene, unreacted diisopropylbenzene and a 1,3-di-(2-hydroxy-2-propyl)benzene by-product, an extracting step in which said oxidized solution is subjected to an extraction using an aqueous alkali solution to produce an aqueous layer containing 1,3-di-(2-hydroperoxy-2-propyl)benzene, 3-(2-hydroxy-2-propyl)-1-(2-hydroperoxy-2-propyl)benzene and 1,3-di-(2-hydroxy-2hydroxy-2-propyl)benzene, and an oily layer containing 3-isopropyl-1-(2-hydroperoxy-2-propyl)benzene, 1,3-diisopropylbenzene and 1,3-di-(2-hydroxy-2-propyl)benzene, and a recycling step in which at least part of said oily layer is recycled as a circulating oil back to the starting solution;

further comprising controlling the ratio A/B to 330 or more, wherein A is the weight of the aqueous alkali solution used in the extracting step per unit time and B is the weight of 1,3-di-(2-hydroxy-2-propyl)benzene by-product produced in the oxidizing step and extracting step per unit time, such that the accumulated equilibrium concentration of 1,3-di-(2-hydroxy-2-propyl)benzene in the circulating oil is 3.6% by weight or less, wherein the weight percentage is based on the total weight of the circulating oil.

3. The process according to claim 1 or 2, wherein the ratio A/B is 400 or more, wherein A is the weight of aqueous solution used in the extracting step per unit time and B is the weight of 1,3-di-(2-hydroxy-2-propyl)benzene produced in the whole system per unit time.

4. The process according to claim 1 or 2, wherein the aqueous layer obtained in the extracting step with an aqueous solution is subjected to extraction with methyl isobutyl ketone to produce a methyl isobutyl ketone layer containing 1,3-di-(2-hydroperoxy-2-propyl)benzene and an aqueous layer.

5. The process according to claim 1 or 2, wherein the aqueous layer obtained in the extracting step with an aqueous solution is subjected to extraction with methyl isobutyl ketone to produce a methyl isobutyl ketone layer containing 1,3-di-(2-hydroperoxy-2-propyl)benzene and an aqueous layer, and said aqueous layer is recycled back to the extracting step with an aqueous solution.

* * * * *